US007919442B2

(12) United States Patent
Aramaki et al.

(10) Patent No.: US 7,919,442 B2
(45) Date of Patent: Apr. 5, 2011

(54) PROCESS FOR PREPARING MULTIPHASE TOILET SOAP

(75) Inventors: Nancy Sayuri Kanegae Aramaki, Jundiaí (BR); Simone Flauto, São Paulo (BR); Tadeu De Oliveira Marin Chicol, Ribeirão Pires (BR)

(73) Assignee: Natura Cosmeticos S.A., Sao Paulo SP (BR)

( * ) Notice: Subject to any disclaimer, the term of this patent is extended or adjusted under 35 U.S.C. 154(b) by 469 days.

(21) Appl. No.: 10/599,238

(22) PCT Filed: Mar. 23, 2005

(86) PCT No.: PCT/BR2005/000037
§ 371 (c)(1),
(2), (4) Date: Jul. 21, 2008

(87) PCT Pub. No.: WO2005/093033
PCT Pub. Date: Oct. 6, 2005

(65) Prior Publication Data

US 2008/0280798 A1 Nov. 13, 2008

(51) Int. Cl.
*A61K 7/50* (2006.01)

(52) U.S. Cl. ......... 510/141; 510/451; 510/458; 510/459

(58) Field of Classification Search ........................ None
See application file for complete search history.

(56) References Cited

U.S. PATENT DOCUMENTS 3,673,294 A 6/1972 Matthaei
4,094,946 A 6/1978 Finkensiep et al.
4,096,221 A 6/1978 Fischer et al.
4,127,372 A 11/1978 Perla et al.
4,196,163 A 4/1980 Finkensiep et al.
4,310,479 A 1/1982 Ooms et al.
4,405,492 A 9/1983 Nyquist et al.
6,174,845 B1 1/2001 Rattinger et al.
6,376,441 B1 4/2002 Ross et al.
6,383,999 B1 5/2002 Coyle et al.
6,390,797 B1 5/2002 Myers
6,413,928 B1 7/2002 Painter et al.
6,440,927 B1 8/2002 Painter et al.
6,533,979 B1 3/2003 Lee
6,548,473 B1 4/2003 Jacques Kamiel Thoen et al.
6,555,509 B2 4/2003 Abbas et al.
2002/0077258 A1 6/2002 Sonnenberg et al.

FOREIGN PATENT DOCUMENTS

DE 298 18 996 6/1999
EP 0 545 716 6/1993

OTHER PUBLICATIONS

International Preliminary Report on Patentability for PCT/BR2005/000037 completed Mar. 3, 2006.
International Search Report for PCT/BR2005/000037 completed May 30, 2005.

*Primary Examiner* — Necholus Ogden, Jr.
(74) *Attorney, Agent, or Firm* — Alston & Bird LLP

(57) ABSTRACT

The present invention relates to a process of preparing bar toilet soap, composed of multiple phases, at least one of them being an opaque phase and at least one being a translucent phase. The translucent phase and the opaque phase(s) are mixed during the process, wherein the translucent phase is incorporated into the opaque phase during the extrusion of this second phase, giving rise to a toilet soap in which one of the phases predominate and the other appears as stripes dispersed in the first one.

10 Claims, 2 Drawing Sheets

PROCESS FOR PREPARING MULTIPHASE TOILET SOAP

This application claims the priority of Brazilian patent case No. PI0401785-4 filed on Mar. 25, 2004 which is hereby incorporated by reference.

The present invention relates to a process for preparing a bar toilet soap composed of multiple phases, at least one phase being opaque and at least one phase being translucent. The translucent phase(s) and the opaque phase(s) are mixed during the process, giving rise to a toilet soap wherein one of the phases predominates and the other appears as stripes dispersed in the former.

DESCRIPTION OF THE PRIOR ART

At present, formulations of bar toilet soaps are known, which are composed of multiple phases, and it is most common to find toilet soaps having only two phases. Various manufacture methods are used for preparing them. Documents of the prior art that disclose formulations of toilet soaps as described above are cited below.

Some documents disclose toilet soaps having two phases clearly separated from each other, either due to the manufacture process or due to a physical structure separating them, namely:

Document U.S. Pat. No. 6,555,509 discloses a multiphase toilet article, the phases of which are separated by a membrane, as well as the processes for producing this article. Each phase comprises a different composition. The membrane is at least partly water-soluble, and the material employed to prepare it is selected to dissolve or disintegrate as the product is used. This is a toilet soap that has phases completely separated from each other.

Document EP 0545716 describes a soap comprising two phases. This soap has a first portion that is at least translucent and may be transparent, and a second portion that is opaque. Each portion of the soap has at least 80% of its mass composed by the same components, and the phases are joined together in the step of molding the toilet soap, preferably having a curvilinear shape. The process for producing this soap is such that a clear composition is arranged in a mold, partly filling it. Later the opaque composition is arranged in the mold, completing its volume. Theses steps of the process may be inverted. Again, it can be concluded that this is a soap that comprises two phases completely separated from each other.

On the other hand, document U.S. Pat. No. 6,376,441 (corresponding to Brazilian PI 0013372-8) discloses a multiphase molten toilet soap, which has at least one interface that projects along the plane perpendicular to the plane formed by the axles x and y of said toilet soap, and also a process for producing it. The process for producing this toilet soap is continuous, and the cleaning agents comprised within the toilet soap are put into the mold and kept therein until they become hard, being then removed to give way to more molten cleaning agents. The hardened multiphase toilet soap is then ejected from the mold. This mold comprises said interface, which separates the phases until they are completely hardened.

Document U.S. Pat. No. 6,533,979 discloses a method for producing a soap by using an equipment for molding said soap that comprises two connected tubes, through which two different soap materials of contrasting colors pass and are poured into a mold, resulting in the finished soap. The soap body has stripes from one face to the other in its cross section, that is to say, one phase is injected into the other. There is not mixing between them; the phases are intercalated.

Documents U.S. Pat. No. 6,413,928 and U.S. Pat. No. 6,440,927 (corresponding to Brazilian documents PI 9813201-6 and PI 9814022-1) deal, respectively, with a multiphase soap and a process for preparing it, which comprise the steps of: a) molding a soap body compressing a granular mixture of detergent, said body having a first surface, said first surface having at least one mold and said mixture comprising at least one detergent active agent; b) preparing a gelatinous mixture under constant stirring and pouring it into the mold, forming a gelatinous portion; and c) hardening and curing the gelatinous portion, which results in a multiphase soap. Again, it is noted that the phases remain separated from each other.

Document US 2002/0077258 (corresponding to Brazilian document PI 0114018-3) discloses multiphase soaps in which the phases are easily visible when the soap is seen from above or from the sides. Various arrangements of the phases are foreseen, the amount of each of them varying as Well. The phases are arranged in, layers and kept visibly separated from each other.

Further, document U.S. Pat. No. 6,548,473 (corresponding to Brazilian document PI 9807007-0) discloses a multilayer bar soap comprising a solid compressed body having, at least inside it, a mold and at least one non-compressed and non-encapsulated portion arranged within said mold, and comprising at least one active agent.

Document U.S. Pat. No. 6,174,845 (corresponding to Brazilian document PI 9808438-0) describes toilet-soap compositions in which an emollient composition is added to the base toilet-soap composition during the extrusion process, which result in a second phase. The second phase, however, is arranged separately from the first one.

Document U.S. Pat. No. 6,383,999 (corresponding to Brazilian PI 0108259-0) discloses a multiphase toilet soap comprising a plurality of phases of cleaning materials. Preferably, the adjacent phases have different concentrations of components and all the phases have a similar cleaning base. These components are emollients, moisturizing agents, nutrients, anti-aging agents, etc.

Still other documents describe a process of introducing additives in the bar toilet-soap mass so as to form a dispersed stripes in it, as can be inferred from the documents cited below:

Document U.S. Pat. No. 6,390,797 (corresponding to Brazilian PI 0000839-7) deals with an apparatus and a process for introducing various additives in solid form to the soap mass in order to produce bar soaps. These soaps have a multicolored and marbled appearance. Soap granulates having a determined color are introduced in the soap body. Further, colored granulates may be introduced by means of a special apparatus that controls the rate of flow of such elements and ensures that they will be directly introduced in a chamber formed by a flight of helical screw.

Finally, documents U.S. Pat. No. 4,096,221, U.S. Pat. No. 4,094,946, U.S. Pat. No. 4,196,163, U.S. Pat. No. 4,634,654, and U.S. Pat. No. 4,127,372 describe processes and apparatuses for introducing colors in the toilet soaps by using additives, which results in colored stripes.

SUMMARY OF THE INVENTION

The present invention has the objective of providing a process of preparing multiphase toilet soaps that comprises the following steps:

a—adding, in sequence, the following components:

i—base toilet-soap mass, opacifying agent and chelating agent ii—at least one surfactant and emollient iii—a chelating agent; and iv—essence and anti-oxidizing agent to a Mixer (1) connected, at intervals of at least 10 minutes between the additions of each of the groups (i) to (iv) above;

b—mixing, during an interval of time sufficient to achieve total homogenization of the components;

c—introducing the mixture obtained in item b in a roller mill (not shown), according to a lamination velocity until homogenization is achieved;

d—transferring by conveyor belts, the laminated mass to an Extruder (9) and extruding it once through the preliminary Trafila (8);

e—during the preparation of the extruded mass of the opaque phase, adding a translucent phase by means of a conveyor belt or a dosing equipment (6), with controlled addition time, according to the appearance wished to be achieved;

f—introducing the mixture containing the opaque and translucent phases in a final Trafila (7), at a temperature ranging from 60 to 80° C., at a velocity suitable for obtaining a homogeneous and constant product;

g—introducing the extruded mass (5) obtained in item f in a cutter (not shown), cutting it in compact form and in the appropriate size compatible with the size of the mold;

h—molding the extruded and cut mass in a press.

By using this process, a toilet soap having at least two mixed and well-defined phases (opaque and translucent) is obtained, which do not separate from each other during the use of the toilet soap.

The present invention has also the objective of providing a multiphase toilet soap prepared according to the process aimed.

BRIEF DESCRIPTION OF THE FIGURES

The present invention will now be described in greater detail with reference to an embodiment represented in the drawings. The figures show.

DETAILED DESCRIPTION OF THE INVENTION

Figure 1:
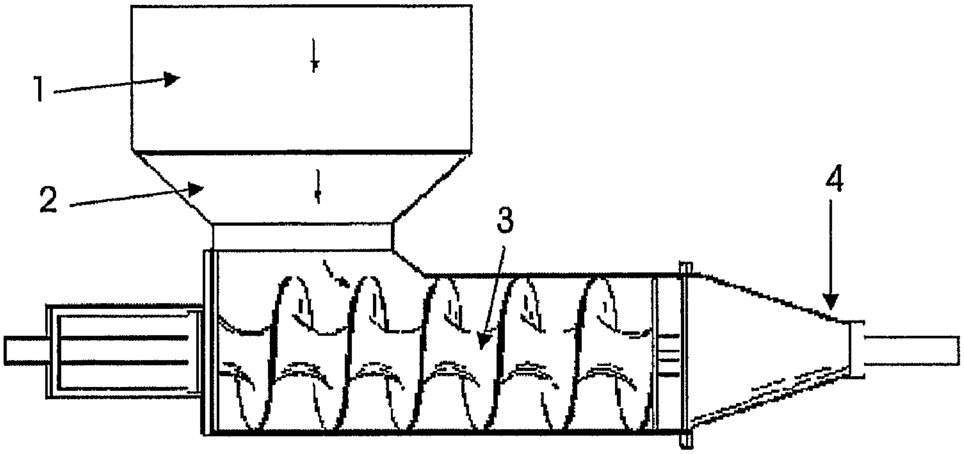
FIG. 1 illustrates the equipment used for preparing the translucent phase to be inserted into the multiphase toilet soap prepared according to the present invention.

The present invention describes a process for the manufacture/preparation of a bar toilet soap, preferably of vegetable base, composed of at least two phases, one of them being opaque and the other being translucent (the translucent phase is that which permits passage of a certain amount of light), wherein the translucent phase is incorporated into a intermediate step of the process of making the opaque phase, with the use of a dosing belt of device.

The two types of the phase present in the multiphase toilet soap should be compatible, so that there will be consistency between them. Further, on the one hand the mixture should be stable, maintaining the aspect of each of the phases and, on the other hand, there should be no homogenization of the mixture of the two phases, so that the presence of both phases will be clear.

The composition of the translucent phase comprises at least base toilet-soap mass, preferably of vegetable base (containing more water-soluble salts of carboxylic acids), translucency promoting agents, a chelating agent, a moisturizing agent, essence, dye. Optionally, emollient and actives may be added.

On the other hand, the composition of the opaque phase comprises base toilet-soap mass, preferably of vegetable base (containing water-soluble salts of carboxylic acids, an opacifying agent, a chelating agent, an emollient, essence, dye and an anti-oxidizing agent. Optionally, actives may be added.

In the composition of the multiphase toilet soap of the present invention, the amount of the translucent phase may range from 5.0 to 95.0%, preferably from 10.0 to 20.0% and the amount of opaque phase may range from 5.0 to 95.0%, preferably from 80.0 to 90.0% by weight, based on the total weight of the composition.

The options of components that are preferably used in the composition of each of the phases are described below. However, other components of each of the classes below, commonly added to the composition of toilet soaps of the prior art, may be added.

Base Toilet-Soap Mass

Preferably, the toilet-soap base for the composition of the multiphase toilet soap of the present invention is constituted by components of vegetable origin. However, a mass containing components of animal origin, usually found in toilet-soap compositions of the prior art, may be added.

In the constitution of the base toilet-soap mass, water-soluble salts of carboxylic acids are preferably used. Preferred examples of carboxylic acids the salts of which are ideal for the composition of the base toilet-soap mass are those derived from triglyceride and oils, such as animal tallow, coco-nut oil, babassu oil, oils derived from palm, among other vegetable oils.

Also, synthetic bases may be used, such as cocoyl, sodium isocyanate and sodium lauryl sarcosinate.

Translucency Promoting Agent

The translucent phase is that which permits passage of a certain amount of light. This phase will be incorporated into the opaque phase, according to the process of preparing the present invention, in order to compose the multiphase toilet soap.

In order to obtain a translucent toilet-soap mass, at least one translucency promoting agent is used as, for example, sugars, preferably refined sugar, vegetable and animal stearic acid with trietanolamine, animal or vegetable glycerin, sodium chloride, propyleneglycol and sorbitol.

Besides adding translucency promoting agents, suitable mixers and/or homogenizers are used so as to bring about the alignment of the molecules due to the mechanical strain, which entails the passage of light.

In the preferred embodiments of the present invention, refined sugar, vegetable glycerin, vegetable stearic acid with trietanolamine, propyleneglycol, sodium chloride are opted with the function of translucency promoting agents.

Chelating Agent

The chelating agent exhibits the property of sequestering ions from the solution, that is to say, it is capable of sequestering calcium atoms and magnesium atoms, but preferably exhibits selectivity for binding to ions such as iron, manganese and copper ions. In this sense, its function in the composition of the multiphase toilet soap described herein is to control a possible oxidation action, which might occur and also to provide stability in storage of the cosmetic compositions of the present invention.

Preferred chelating agents to be added to the composition of the multiphase toilet soap of the present invention are:

etidronic acid, citric acid, ethylenediaminetetraacetic acid (EDTA), ethylene diamine phosphonic acid and hydroxyethane diphosphonic acid.

In the preferred embodiments of the present invention, etidronic acid and tetrasodic EDTA are selected to act as chelating agents.

Moisturizing Agent

The moisturizing agent in the composition of the multiphase toilet soap promotes the retention of water in the skin of the user, that is to say, it provides water to the skin and also presents the loss of water of the skin. The moisturizing agent further aids in increasing the effectiveness of the emollient, in case this component is present, reduces the staling of the skin and improves the sensitivity of the skin.

Some examples of moisturizing agents that may be added to the composition of the multiphase toilet soap of the present invention are: glycerol, ethoxylated glycerol, propoxylated glycerol, sorbitol, ethoxylated methylglucose, hydroxypropyl sorbitol, among others, glycerin and vegetable glycerin, and salts of lactate, propyleneglycol, butyleneglycol, polyethyleneglycol, urea, natural oils such as oils and waxes and mixtures thereof.

In the preferred embodiments of the preparation of the multiphase toilet soap of the present invention, propyleneglycol and vegetable glycerin are used as moisturizing agent.

Essence

It is optional to add to the composition of the multiphase toilet soap essence selected from a range of possible substances. Essences that are usually added to compositions of toilet soap of the prior art are employed.

The essence or fragrance may be added both to the opaque phase and to the translucent phase.

Active

The following actives may be added: lipophilic or hydrophilic components such as seaweed extracts, combination of palmitoil hydroxypropyl triommonium aminopectin, glycerin crospolymer, lecitin and grape-seed oil, bisabolol (anti-inflammatory active), D-pantenol (conditioning active), tocoferol (vitamin E), ascorbic acid (vitamin C).

Vegetable oils or extracts may be added such as chamomile extract, rosemary extract, thyme extract, calendula extract, carrot extract, common-juniper extract, Surinam cherry extract, guarana extract, cupuaçu butter, carap-nut oil, among others.

Further, exfoliating microspheres of vegetable exfoliants may be added in order to impart an additional function to the multiphase toilet soap.

The active components may be added in both the opaque phase and translucent phase.

Anti-Oxidizing Agent

The anti-oxidizing agent acts in protecting the composition of the toilet soap from oxidizing actions.

Compounds with anti-oxidizing properties that may be added to the variations of composition of the multiphase toilet soap of the present invention are: sulfites, ascorbates, amino acids (for example, glycine, histidine, tyrosine and triptophane), imidiazoles, urocanic acid and derivatives thereof, peptides (for example, D, L-carnosin, D-carnosine and L-carnosin), anserine, carotenoids, carotenes and derivatives thereof (for example, alpha-carotene and beta-carotene), lycopen and derivatives thereof, lipophilic substances such as butyl hydroxytoluene (BHT), butyl hydroxyanisol (BHA), tetradibutyl pentaeritryl hydroxyhydroxinamate, hydrophilic substances such as phenoxyethaneol, benzyl alcohol, methylparaben, propylparaben, hydantoins.

In the preferred variations of the composition of the multiphase toilet soap of the present invention, butylhydroxytoluene (BHT) is used as an anti-oxidizing agent, especially in the constitution of the opaque phase.

Opacifying Agent

This component will be added exclusively to the opaque phase of the multiphase toilet soap. Preferred embodiments of opacifying agents to be added to the composition of the multiphase toilet soap of the present invention are titanium dioxide, alumina, zinc oxide, calcium carbonate or mixtures of inorganic minerals. However, other opacifying components usually employed in compositions of toilet soaps of the prior art may be added.

The opaque phase of the multiphase toilet soap of the present invention comprises an opacifying agent in an amount ranging from 0.1 to 5.0%, preferably from 0.3 to 0.9% by weight, based on the total weight of the composition.

Surfactants

Preferred embodiments to be used either in isolation or in conjunction in the composition of the multiphase toilet soap as a surfactant, especially in the opaque phase, are alkylglucosides, decyl polyglucose such as decyl polyglucose 2000, sodium cocoil isotianate, sodium lauryl sulphosuccinate.

Dye

Any dyes found in compositions of toilet soap of the prior art may be used. A few examples of such dyes are: natural carmine, chlorophyll, curcumin, annatto, dyestuffs of vegetable origin, caramel dyestuff and FD&C coloring agents.

Different kinds of dyestuffs may be used in the same toilet soap, imparting a broader range of colors to the product, especially when the product contains more than one translucent phase.

Emollient

The function of emollients in compositions intended for skin care is to add or replace lipids and natural oil to the skin.

Some examples of emollients that may be added to the composition of the multiphase toilet soap are:

conventional lipids such as waxes and other water-soluble components, in addition to polar lipids, mineral oil, natural oils such as esters, silicone oils such as dimethicone copolyol and silicone fluid, soybean lecitin, polyunsaturated fatty acids, lanoline and derivatives thereof such as lanoline and lanoline fatty acids and glycols such as glycerin and propyleneglycol. Some natural oils that may be used are derived from damson seed, sesame seeds, soybean, pea-nut, coconut, olive, cocoa-nut butter, almond, carnauba, cotton seed, rice bran, peach seed, jojoba, macadamia, coffee, grape feed, pumpkin seed, among others and mixtures thereof.

Some ethers and esters may also be used in the function of emollients, as for example dicaprylic ether, cetyl lactate, isopropyl palmitate, $C_{12-15}$ alkyl benzoate, isopropyl myristate, isopropyl isononate and combinations thereof.

In the preferred embodiments of the present invention, mineral oil and soybean lecitin are used as emollient.

By using the above-described options, it can be concluded that the constitution of each of the phases may be different, since they may contain different components without impair the final result of the product.

Other components may also be added in order to impart some further characteristic still not present in the composition of the multiphase toilet soap, for example exfoliant and antimicrobial agents.

Process for Preparing the Multiphase Toilet Soap

Figure 3:
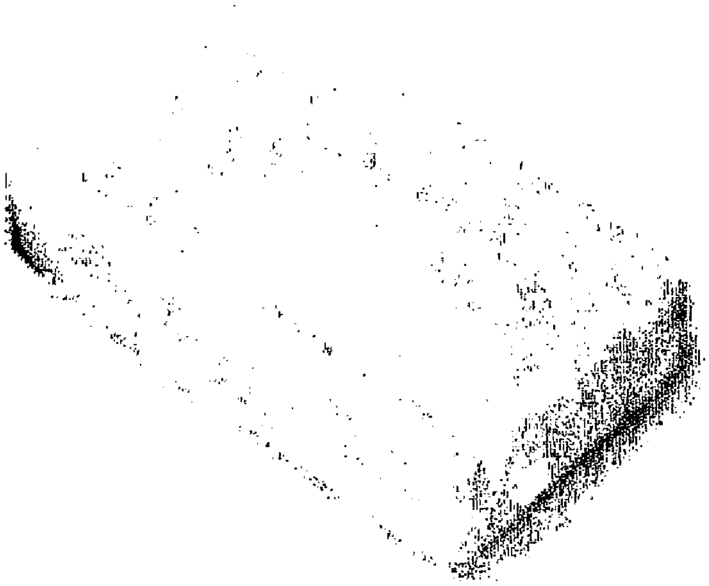
FIG. 3 is a perspective view of the multiphase toilet soap prepared according to the present invention.
Figure 4:
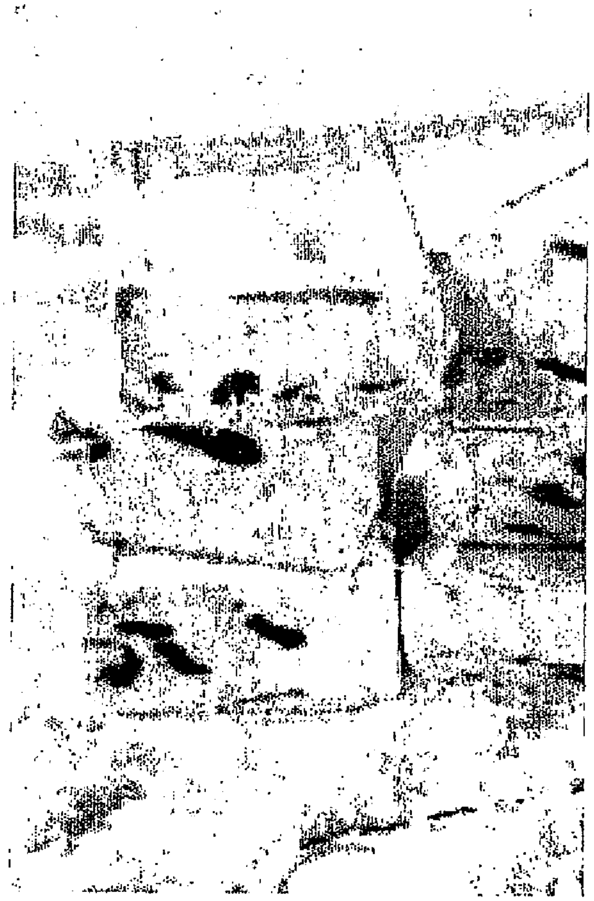
FIG. 4 is a cross-sectional view of a multiphase toilet soap prepared according to the present invention.

The process of preparing the multiphase toilet soap is, in summary, the mixing of the components of the two opaque and translucent phases, so that the translucent phase will be incorporated into the opaque phase during the extrusion of this second phase, as can be seen in FIGS. 3 and 4.

The translucent phase is obtained by using the adequate components, plus application of an intensive and effective mechanical work, preferably by using a Sigma mixer and an extruder, which contributes to achieving the homogenization and stabilization of the Beta crystalline structure. As a result of this sum of factors, a product with translucent appearance is obtained.

On the other hand, the opaque phase is equivalent to a mass of an ordinary toilet soap in the final extrusion step.

In the composition of the multiphase toilet soap, the amount of translucent phase may range from 5.0 to 95.0% by weight, preferably from 10.0 to 20.0% and the amount of opaque phase may range from 5.0 to 95.0% by weight, preferably from 80.0 to 90.0%, based on the total weight of the composition.

A. Preparation of the Translucent Phase of the Multiphase Toilet Soap

TABLE 1

Steps of the Process of Preparing the Translucent Phase

| Steps of the process | Components corresponding to each step |
|---|---|
| 1 | Base Toilet-Soap Mass<br>Moisturizing agent(s)<br>Emollient(s)<br>Chelating agent(s) |
| 2 | Translucency Promoting Agent(s)<br>Chelating agent |
| 3 | Translucency Promoting Agent(s) |
| 4 | Translucency Promoting Agent(s) |
| 5 | Essence<br>Dyestuffs |

The process for preparing the translucent phase present in the multiphase toilet soap, illustrated in FIG. 1, comprises the following steps (the description relates to the preparation of a translucent phase, but there may be more than one translucent phase in the same toilet soap, which will be prepared according to the same process):

a—adding the components of Step 1 in a Sigma G. Mazzoni Mixer (1); mixing, for a period of time sufficient for achieving total homogenization among the components of this phase; usually, the time necessary for this homogenization is of about 20 minutes (another mixer that brings about the same homogenization result achieved by using the Sigma G. Mazzoni Mixer may be used);

b—introducing the mixture obtained in step a—in a Mazzoni Extruder (2) and extruding it once through the Trafila (3) and returning to the Mixer (1) (just as in step a—, other pieces of equipment (extruder, trafila and mixer) that bring the same result achieved by using the above-cited preferred pieces of equipment may be utilized);

c—adding the components of Step 2 in the Mixer (1); mixing, for a period of time sufficient to achieve total homogenization of the components of this phase, preferably for about 20 minutes;

d—introducing the mixture obtained in step c—in a Mazzoni Extruder (2) and extruding it once through the Trafila (3) and returning to the Mixer (1);

e—heating at least one translucency promoting agent of Step 3, other than translucency promoting agent(s) added in step c—, at a temperature of 50° C. and adding this partial composition in the Mixer (1); mixing for a period of at least 15 minutes;

f—adding at least one translucency promoting agent of Step 4, other than the translucency promoting agent(s) added in step e—, in the Mixer (1); mixing this partial composition for about 40 minutes or until total homogenization of the components is achieved and it reaches a translucent appearance;

g—introducing the mixture obtained in step f—in the Mazzoni Extruder (2) and, extruding it once through the Trafila (3) and returning to the Mixer (1);

h—adding the components of Step 5 in the Mixer (1); mixing this partial composition for about 15 minutes or until total homogenization of the components of this phase and stabilization of the Beta crystalline structure are achieved;

i—introducing the mixture obtained in step h—in the Mazzoni Extruder (2);

j—cutting the bars into pieces (noodles) (4), preferably ranging from 3.0 to 5.0 cm in length.

Optionally, actives may be added in Stage 1 of this process step.

The translucent phase should be removed from the upper part of the extruder in sizes ranging from 0.5 to 15.0 cm, preferably from 3.0 to 5.0 cm in length, and it should be reserved for being added to the multiphase toilet soap during the preparation of the opaque phase.

The translucent phase may be manufactured 30 days in advance, preferably from 3 to 5 days.

B. Preparation of the Final Multiphase Toilet Soap

TABLE 2

Steps of the Process and Components of the Opaque Toilet Soap

| Steps of the Process | Components corresponding to each step of the process |
|---|---|
| 1 | Base Toilet-Soap Base<br>Opacifying agent<br>Chelating agent |
| 2 | Surfactants<br>Emollient |
| 3 | Chelating agent |
| 4 | Essence<br>Anti-oxidizing agent |

Figure 2:
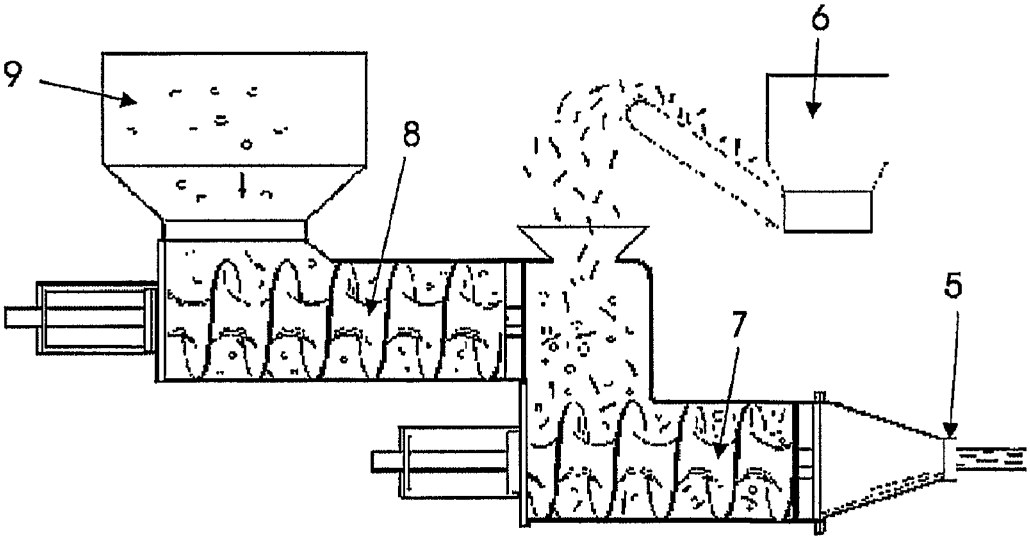
FIG. 2 illustrates the equipment used for preparing the multiphase toilet soap prepared according to the present invention.

The process for preparing the multiphase toilet soap, illustrated in FIG. 2, comprises the following steps:

a—adding the components of Steps 1, 2, 3 and 4 listed above (opaque phase) in a Sigma G. Mazzoni Mixer (not shown), connected, at intervals of at least about 10 minutes between the additions of each group of components of the steps (another mixer that brings about the same homogenization result achieved by using the Sigma G. Mazzoni Mixer may be used);

b—mixing, for about 15 minutes or until total homogenization of the components is achieved;

c—introducing the mixture obtained in step b—in a roller mill (not shown) according to an adequate rolling velocity; the rolling velocity is that usually employed for preparing toilet soaps of the prior art; optionally, the mixture may be introduced in the Mill more than once, until it takes on the form of a homogeneous mass, wherein all the components are dispersed; as a result, a rolled mass with about 0.2 mm in thickness is obtained;

d—transferring, by means of conveyor belts (not shown), the rolled mass to a Mazzoni Extruder (9) and extruding it once through the preliminary Trafila (8) (just as in step a—, other pieces of equipment (extruder and trafila) that bring about the same result obtained by using the above-cited preferred pieces of equipment may be used);

e—during the preparation of the extruded mass of the opaque phase, the translucent phase is added by using a conveyor belt that acts as a dosing equipment (6) with controlled addition time, according to the appearance wished to be obtained; optionally, this step may be repeated in order to add more than one translucent phase;

f—introducing the mixture containing the opaque and translucent phases in the final Trafila (7), at a temperature ranging from 60 to 80° C., at a velocity adequate for obtaining a homogeneous and constant product;

g—introducing the extruded mass obtained in item f—in an automatic cutter (not shown), cutting it in compact shape in the adequate size, compatible with the size of the mold;

h—molding the extruded mass in a press (not shown);

i—removing the trims that may be present on the molded toilet soap, which can be re-used by means of a continuous process with conveyor belts that transfer the trims to the Mazzoni Extruder (9).

The dosing equipment (6) is preferably constituted by a conveyor belt with controlled velocity, which carries the pieces (noodles) of the translucent phase from the funnel-shaped deposit to the mixing point of the final extruder. The velocity of addition of the translucent phase should be controlled according to the appearance wished to be achieved.

A preferred embodiment having been described, it should be understood that the scope of the present invention embraces other possible variations, being limited only by the contents of the accompanying claims, which include the possible equivalents.

Examples of Composition of the Translucent Phase and Opaque Phase Comprised in the Multiphase Toilet Soap Example 1

Formulations of the Translucent Phase a—adding the base toilet-soap mass, vegetable glycerin, propyleneglycol, etidronic acid, actives in the Sigma G. Mazzoni Mixer (1); mixing for about 20 minutes until total homogenization is obtained among the components of this step;

b—introducing the mixture obtained in step a—in the Mazzoni Extruder (20 and extruding it through the Trafila (3) and returning to the Mixer (1);

c—adding refined sugar, sodium chloride, tetrasodium EDTA in the Mixer 91); mixing for about 20 minutes until total homogenization among the components of this step is achieved;

d—introducing the mixture obtained in step c—in the Mazzoni Extruder (2) and extruding it once through the Trafila (3) and returning to the Mixer (1);

e—heating the vegetable stearic acid up to a temperature of 50° C. and adding this partial composition in the Mixer (1); mixing for about 15 minutes;

f—adding trietanolamine in the Mixer (1); mixing this partial composition for about 40 minutes until total homogenization of the components is achieved and the composition takes on the translucent appearance;

g—introducing the mixture obtained in step f—in the Mazzoni Extruder (2) and extruding it once through the Trafila (3) and returning to the Mixer 91);

h—adding essence and dyestuffs in the Mixer (1). Mixing this partial composition for about 15 minutes until total homogenization of the components of this phase is achieved, as well as the stabilization of the Beta crystalline structure;

i—introducing the mixture obtained in step h—in the Mazzoni Extruder (2);

j—cutting the bars into pieces (noodles) (4) of about 3.0 to 5.0 cm in length.

| Ingredients | Formula 1 - % weight | Formula 2 - % weight |
|---|---|---|
| Base Toilet-Soap Mass | 82.00 | 82.90 |
| Refined Sugar | 6.00 | 5.00 |
| Vegetable Glycerin | 4.00 | 5.00 |
| Essence | 1.70 | 1.70 |
| Trietanolamin | 1.60 | 1.50 |
| Vegetable Stearic Acid | 1.50 | 1.50 |
| Propyleneglycol | 1.30 | 1.00 |
| Sodium Chloride | 1.00 | 0.50 |
| Active | 0.50 | 0.50 |
| Dyestuffs | 0.36 | 0.36 |
| Etidronic Acid | 0.02 | 0.02 |
| Tetrasodium EDTA | 0.02 | 0.02 |

Example 2

Formulations of the Opaque Phase a—adding the base toilet-soap mass, etidronic acid, titanium dioxide, decyl polyglucose 2000, mineral oil, soybean lecitin, active, tetradisodium EDTA, essence and BHT (opaque phase) (in the Sigma G. Mazzoni Mixer turned on) at intervals of 10 minutes between the steps;

b—mixing for about 15 minutes until total homogenization of the components is achieved;

| Ingredient | Formula 1 - % weight | Formula 2 - % weight |
|---|---|---|
| Base Toilet-Soap Mass | 93.80 | 94.60 |
| Essence | 1.70 | 1.70 |
| Decyl polyglucose 2000 | 1.50 | 1.00 |
| Mineral Oil | 1.40 | 1.00 |
| Titanium Dioxide | 0.50 | 0.60 |
| Soybean Lecitin | 0.50 | 0.50 |
| Active | 0.50 | 0.50 |
| BHT | 0.05 | 0.05 |
| Etidronic acid | 0.03 | 0.03 |
| Tetrasodium EDTA | 0.02 | 0.02 |

After preparing the above-described phases, the general process of joining the opaque and translucent phases is executed:

c—introducing the mixture obtained in step b—in the roller Mill according to a conventional rolling velocity;

d—transferring, on conveyor belts, the rolled mass to the Mazzoni Extruder (9) and extruding it once through the preliminary Trafila (8);

e—during the preparation of the extruded mass of the opaque phase, the translucent phase is added by means of a conveyor belt or by means of a dosing equipment (6), with controlled addition time, according to the appearance which one wishes to achieve;

f—introducing the mixture containing the opaque and translucent phases in the final Trafila (7), at a temperature ranging from 60 to 80° C., at a velocity adequate for obtaining a product with homogeneous and constant consistency;

g—introducing the extruded mass obtained in step f—in the automatic cutter (5), cutting it in compact form in the adequate size, compatible with the size of the mold;

h—molding the extruded mass in the press;

i—removing the trims that may be present on the molded toilet soap, which can be re-used by means of a continuous process with conveyor belts that carry the trims to the Mazzoni Extruder (9).

The invention claimed is:

1. A process of preparing multiphase toilet soap, the process comprising the following steps:

a—adding, in sequence, the components:

i—base toilet-soap mass, opacifying agent and chelating agent, ii—at least one surfactant and emollient, iii—a chelating agent; and iv—essence and anti-oxidizing agent, in a turned-on Mixer, at intervals of at least 10 minutes between the additions of each of the above groups (i) to (iv);

b—mixing for a period of time sufficient to achieve total homogenization of the components;

c—introducing the mixture obtained in step b—in a roller mill according to a rolling velocity until homogenization is achieved;

d—transferring, on conveyor belts, the rolled mass obtained in step c—to an Extruder and extruding it once through a preliminary Trafila to form an extruded mass of an opaque phase;

e—during the preparation of the extruded mass of the opaque phase, adding a translucent phase by means of a conveyor belt that acts as a dosing equipment;

f—introducing the mixture containing the opaque and the translucent phases into a final Trafila operating in an open atmospheric environment, the introducing of the mixture occurring at a temperature ranging from 60 to 80° C., and at a velocity adequate for obtaining a heterogeneous and constant product;

g—introducing the extruded mass obtained in step f—in a cutter to form a cut mass; and h—molding the cut mass in a press.

2. A process of preparing multiphase toilet soap according to claim 1, the process further comprising the additional step of removing the trims present on the molded toilet soap and re-using them by means of a continuous process with conveyor belts that transfer the trims to the Extruder.

3. A process of preparing multiphase toilet soap according to claim 1, wherein the translucent phase is prepared according to the following steps:

a—adding the base toilet-soap mass, moisturizing agent, emollient agent and chelating agent in a Mixer and mixing for a period of time sufficient to achieve total homogenization of the components;

b—introducing the mixture obtained in step a—in an Extruder and extruding it once through a Trafila and returning to the Mixer;

c—adding at least one translucency promoting agent and a chelating agent in the Mixer and mixing for a period of time sufficient to achieve total homogenization of the components;

d—introducing the mixture obtained in step c—in the Extruder and extruding it once through the Trafila and returning to the Mixer;

e—heating at least one translucency promoting agent other than the translucency promoting agent(s) added in step c—, at a temperature of 500 C and adding this partial composition in the Mixer and mixing for about at least 15 minutes;

f—adding at least one translucency promoting agent other than the translucency promoting agent(s) added in step e—in the Mixer; mixing this partial composition for about 40 minutes or until partial homogenization of the components is achieved and the composition takes on the translucent appearance;

g—introducing the mixture obtained in step f—in the Extruder and extruding it once through the Trafila and returning to the Mixer;

h—adding essence and dyestuffs in the Mixer and mixing this partial composition for a period of time sufficient to achieve partial homogenization of the components of this phase, as well as stabilization of the Beta crystalline structure;

i—introducing the mixture obtained in step h—in the Extruder to form a plurality of bars; and j—cutting the plurality of bars into pieces of about 3.0 to 5.0 cm in length.

4. A process of preparing multiphase toilet soap according to claim 1, wherein the mixer is a Sigma G. Mazzoni mixer.

5. A process of preparing multiphase toilet soap according to claim 1, wherein the extruder is a Mazzoni extruder.

6. A process of preparing multiphase toilet soap according to claim 1, wherein the extruder is a Mazzoni extruder.

7. A process of preparing multiphase toilet soap according to claim 1, wherein at least one active is added to the composition.

8. A process according to claim 1, wherein, in the step (e), more than one translucent phase is added to the opaque mass that is being extruded.

9. Multiphase toilet soap characterized by being prepared according to the process as defined in claim 1 and having visible speckles.

10. A process of preparing multiphase toilet soap according to claim 1, wherein the conveyor belt that acts as a dosing equipment is operated during step e—at a controlled rate, for a controlled time to achieve a desired consistency of the obtained mixture containing the opaque and the translucent phases.

* * * * *

UNITED STATES PATENT AND TRADEMARK OFFICE

CERTIFICATE OF CORRECTION

PATENT NO. : 7,919,442 B2
APPLICATION NO. : 10/599238
DATED : April 5, 2011
INVENTOR(S) : Aramaki et al.

It is certified that error appears in the above-identified patent and that said Letters Patent is hereby corrected as shown below:

On the title page, please insert Item (30):

--(30) Foreign Application Priority Data

March 25, 2004 (BR) ..................PI0401785-4--

Signed and Sealed this
Seventh Day of February, 2012

David J. Kappos
*Director of the United States Patent and Trademark Office*